(12) United States Patent
Nelson et al.

(10) Patent No.: US 10,914,847 B2
(45) Date of Patent: Feb. 9, 2021

(54) HIGH RESOLUTION IMAGING SYSTEM FOR DIGITAL DENTISTRY

(75) Inventors: Robert Sigurd Nelson, La Mesa, CA (US); William Bert Nelson, Excelsior, MN (US)

(73) Assignee: Minnesota Imaging and Engineering LLC, Excelsior, MN (US)

(*) Notice: Subject to any disclaimer, the term of this patent is extended or adjusted under 35 U.S.C. 154(b) by 287 days.

(21) Appl. No.: 13/199,612

(22) Filed: Sep. 6, 2011

(65) Prior Publication Data

US 2012/0181437 A1 Jul. 19, 2012

Related U.S. Application Data

(63) Continuation-in-part of application No. 12/930,771, filed on Jan. 18, 2011, now Pat. No. 9,384,864.

(51) Int. Cl.
  *G01T 1/20* (2006.01)
  *A61B 6/00* (2006.01)
  *A61B 6/14* (2006.01)

(52) U.S. Cl.
  CPC .......... *G01T 1/2012* (2013.01); *A61B 6/4216* (2013.01); *A61B 6/14* (2013.01); *A61B 6/4494* (2013.01)

(58) Field of Classification Search
  None
  See application file for complete search history.

(56) References Cited

U.S. PATENT DOCUMENTS

| | | | |
|---|---|---|---|
| 4,160,997 A * | 7/1979 | Schwartz | ........................ 348/66 |
| 4,209,908 A | 7/1980 | Fleer | |
| 4,525,628 A * | 6/1985 | DiBianca | ................ C04B 35/50 |
| | | | 250/361 R |
| 4,560,882 A | 12/1985 | Barbaric et al. | |
| 4,666,037 A | 5/1987 | Weissman | |
| 4,937,453 A | 6/1990 | Nelson | |
| 4,950,907 A | 8/1990 | Kuhn | |
| 5,017,782 A | 5/1991 | Nelson | |

(Continued)

FOREIGN PATENT DOCUMENTS

EP          036309 A2     4/1990

OTHER PUBLICATIONS

Innovation in Reach, Kodak 9000C 3D Panoramic & Cephalometric System, 8 pages from <https://web.archive.org/web/20100105025036/http://kodakdental.com/?cookieCheck=true>.

(Continued)

*Primary Examiner* — Hoon K Song

(74) *Attorney, Agent, or Firm* — Dorsey & Whitney LLP

(57) ABSTRACT

A structured dental x-ray detector implements an array of holes or channels filled with at least one of polycrystalline, amorphous, or nano-particle semiconductor x-ray or gamma ray converter materials. Readout electronics are configured for acquiring and analyzing signals from the detector; e.g., operating in a signal integration or photon detecting mode, or in a photon detecting mode with energy resolution. In dental application, a protective shell or frame can be provided to encapsulate the detector and readout electronics, with a wired or wireless communications link to a computer system configured for image data post-processing and storage of the readout signals, with an electronic display for the image data.

20 Claims, 11 Drawing Sheets

(56) References Cited

U.S. PATENT DOCUMENTS

| | | | |
|---|---|---|---|
| 5,258,145 A | 11/1993 | Nelson | |
| 5,331,166 A * | 7/1994 | Yamamoto | A61B 6/145 |
| | | | 250/368 |
| 5,376,806 A | 12/1994 | Hejazi | |
| 5,912,942 A | 6/1999 | Schick et al. | |
| 6,097,902 A | 8/2000 | Blume | |
| 6,117,471 A | 9/2000 | King | |
| 6,315,444 B1 | 11/2001 | Koren | |
| 6,352,949 B1 | 3/2002 | Willems et al. | |
| 6,474,864 B1 | 11/2002 | Resch et al. | |
| 6,675,518 B1 | 1/2004 | Porteous | |
| 6,827,214 B2 | 12/2004 | Alzner et al. | |
| 6,866,149 B2 | 3/2005 | Alzner | |
| 7,053,396 B2 | 5/2006 | Alzner et al. | |
| 7,247,861 B2 | 7/2007 | Suzuki et al. | |
| 7,465,431 B2 | 12/2008 | Katusic et al. | |
| 7,507,974 B1 | 3/2009 | Neushul | |
| 7,563,026 B2 | 7/2009 | Mandelkern et al. | |
| 7,608,834 B2 | 10/2009 | Boucly et al. | |
| 7,628,537 B2 | 12/2009 | Schulze-ganzlin | |
| 7,649,190 B2 | 1/2010 | Alzner et al. | |
| 7,896,229 B2 | 3/2011 | Crucs et al. | |
| 7,959,354 B2 | 6/2011 | Steward, Jr. et al. | |
| 8,017,906 B2 | 9/2011 | Nelson et al. | |
| 9,384,864 B2 | 7/2016 | Nelson et al. | |
| 2001/0055368 A1 * | 12/2001 | Carroll | 378/189 |
| 2003/0164319 A1 | 9/2003 | Alzner et al. | |
| 2003/0209594 A1 | 11/2003 | Alzner | |
| 2004/0046133 A1 | 3/2004 | Winters | |
| 2004/0164257 A1 | 8/2004 | Sayag | |
| 2005/0232575 A1 | 10/2005 | Koren | |
| 2006/0214109 A1 * | 9/2006 | Bueno | H01L 27/14658 |
| | | | 250/370.11 |
| 2007/0267585 A1 | 11/2007 | Porter et al. | |
| 2008/0017539 A1 | 1/2008 | Alzner et al. | |
| 2009/0136002 A1 | 5/2009 | Schmulenson et al. | |
| 2009/0136003 A1 | 5/2009 | Gestetner | |
| 2009/0166545 A1 | 7/2009 | Mandelkem et al. | |
| 2009/0279661 A1 | 11/2009 | Boucly et al. | |
| 2010/0074401 A1 * | 3/2010 | Kayzerman | A61B 5/682 |
| | | | 378/38 |
| 2010/0171052 A1 | 7/2010 | Thoms | |
| 2010/0177875 A1 | 7/2010 | Steward, Jr. et al. | |
| 2011/0150185 A1 * | 6/2011 | Uzbelger Feldman | A61B 6/14 |
| | | | 378/191 |
| 2011/0164733 A1 | 7/2011 | Steward, Jr. et al. | |
| 2011/0168905 A1 * | 7/2011 | Yabuta | H01L 31/085 |
| | | | 250/370.07 |
| 2012/0001737 A1 | 1/2012 | Berger et al. | |
| 2012/0181437 A1 | 7/2012 | Nelson et al. | |

OTHER PUBLICATIONS

Chen G. et al., Journal of Non-crystalline Solids 352, pp. 610-614, 2006.

Johnson J. et al. J. Am. Ceram. Soc. 90 [3] pp. 693-698, 2007.

Fronk, R.G. et al. "High-efficiency microstructured semiconductor neutron detectors for direct 3He replacement." Nuclear Instruments and Methods in Physics Research A 779, (2015), pp. 25-32.

Rowlands J., Phys. Med. Biol. 47, pp. 123-166, 2002.

Kodak RVG Digital Radiography Systems, Kodak RVG 5100 and 6100 Digital Radiography User's Guide. 39 pages. Dec. 2010.

Edgar A., et al., Current Applied Physics 6, pp. 399-402, 2006.

Turner, "Atoms, Radiation, and Radiation Protection", 2007, pp. 274-296, 3rd Edition, WILEY-VCH Verlag GmbH & Co. KGaA, Germany.

* cited by examiner

HIGH RESOLUTION IMAGING SYSTEM FOR DIGITAL DENTISTRY

CROSS-REFERENCE TO RELATED APPLICATIONS

This application is a continuation-in-part of U.S. patent application Ser. No. 12/930,771, HIGH RESOLUTION IMAGING SYSTEM FOR DIGITAL DENTISTRY, filed on Jan. 18, 2011, issued Jul. 5, 2010, as U.S. Pat. No. 9,384,864, which claims priority to U.S. Provisional Patent Application Ser. No. 61/336,632, filed on Jan. 25, 2010.

FIELD

This invention provides novel high resolution imaging systems and designs for use in digital dentistry that are also suitable for radiation monitoring and related industrial and scientific imaging applications.

BACKGROUND

The dominant intraoral x-ray radiographic imaging system detector for dentistry uses analog x-ray film optically-coupled to an x-ray scintillator screen (a film-screen unit) which is encased in a flexible, sealed (light-tight, impenetrable-to-fluids) soft packet film holder or carrier. The carrier may be made of a material such as molded Styrofoam or a similar lightweight material that is radiographically transparent.

Dental x-ray film-screen units and carriers can be designed to fit a range of patient mouth sizes. The size of the film typically exceeds the size of the x-ray scintillator screen for handling purposes. The x-ray film, once processed, offers excellent spatial resolution with acceptable contrast resolution. The x-ray films can be displayed with an inexpensive light box and copied for distribution.

A typical image acquisition scenario is to position the carrier in the patient's mouth, align the x-ray tube, and expose the x-ray film and x-ray phosphor screen held within the carrier to x-ray radiation. After exposure to x-rays the carrier is taken to a photographic dark room where the film is separated from the carrier by mechanical means and then developed in a film processor. Typically a vendor (for example KODAK) will provide the x-ray film, the film holder or carrier, the film processor and necessary chemicals and a light box for viewing developed films. Processing of films can take several minutes which is rarely an issue since the patient can continue to sit in a chair and read, etc. or other procedures can be initiated before the x-rays are reviewed.

Developed films can be stored as an analog record or digitized and stored as a digital record. Analog film storage and retrieval/transportation expenses may become issues over time. Failure rates due to defective x-ray film are very low if film expiration dates are observed. Well-known limitations of this imaging format include the use of the x-ray scintillator screen which blurs the incident x-ray signal, the limited dynamic range of the film, and possible non-uniformities in the chemical film-development process.

An alternative detector technology to x-ray film is the intraoral digital x-ray camera (which still employees a scintillator screen) that is reusable. It offers acceptable (moderate) spatial resolution and very good contrast resolution (wide dynamic range). The digital readout is available relatively quickly and can be viewed on a monitor or an analog copy can be printed on film. Digital storage and retrieval/transportation are straightforward and cost-effective. Limitations of digital x-ray cameras include high cost per unit (limiting the number of units a typical dental office can own), the size and rigidity of the camera (patient discomfort), the ability to damage the camera physically or by radiation, a cable (communications, power) that sticks out of the patient's mouth (discomfort) and general hygiene issues.

Recently a vendor has made three sizes of digital x-ray cameras available for intraoral radiography, the RVG 6100 System (KODAK), in an attempt to address the limitation imposed by using a single camera size for all applications. X-ray camera sizes are available for pediatric ($22.2 \times 30.8$ mm$^2$), general purpose ($27.5 \times 37.7$ mm$^2$), and bitewing radiographs ($32.2 \times 44.1$ mm$^2$ with resolution limits between 14-20 lp/mm. Note that the active (x-ray sensitive) detector areas are reduced to $17 \times 22$ mm$^2$, $22 \times 30$ mm$^2$ and $27 \times 36$ mm$^2$, respectively, due to packaging requirements that include a protective mount that also provides structural strength, a cable connection, and electronics. Intraoral digital x-ray cameras are often advertised as a means of lowering patient radiation dose relative to x-ray film-based imaging.

Storage phosphor detectors have been used for general diagnostic x-ray radiography since the 1980s, typically in the form of large area rigid plates for applications ranging from chest x-rays to x-ray mammography (Rowlands J., Phys. Med. Biol. 47, pp. 123-166 2002)). A well-known limitation for current implementations of storage phosphor plates used in x-ray mammography is that they offer relatively poor spatial resolution compared to mammography x-ray film-screen units.

Digital dental imaging spatial resolution requirements are comparable or exceed those of digital mammography. Improving spatial resolution typically requires thinner storage phosphor plates (actually screens comprised of a storage phosphor coating on a sheet of plastic, as used in digital dentistry), resulting in reduced x-ray detection efficiency and increased patient x-ray radiation dose. Market demand for digital dentistry systems based on conventional storage phosphor screen technology has been limited compared to CCD and CMOS-based digital camera systems.

More recently, the technologies used to develop ceramic and nanoparticle (and nano-composite) ceramic scintillators for applications such as nuclear medicine and PET scintillators have been applied to produce large area, relatively transparent nanoparticle storage phosphor ceramic plates (also referred to as storage phosphor plates) capable of extremely high spatial resolution (much higher than 20 lp/mm) and excellent contrast resolution for applications such as x-ray mammography (Edgar A., et al., Current Applied Physics 6, pp. 399-402 (2006); Chen G., et al., Journal of Non-crystalline Solids 352, pp. 610-614 (2006); Johnson J., Schweizer S, J. Am. Ceram. Soc. 90 3, pp. 693-698 (2007)). A typical readout mechanism involves scanning the storage phosphor plate with a fine spot optical beam from a source such as a continuous or pulsed optical laser or LED and coupling the fluorescent light (via fiber optics or other conventional optical coupling means) from the discharged storage phosphor plate to an amplified photodetector such as a photomultiplier tube (PMT). The PMT has little or no response to the scanning beam wavelength due to added filtration and photocathode insensitivity at the long wavelengths used for the scanning beam.

A desirable dental x-ray detector would incorporate (or improve on) the favorable properties of both x-ray film-screen and x-ray camera detectors (cost-effective, reliable, reusable, excellent spatial and contrast resolution, large dynamic range, digital readout). In addition, the dental x-ray detector should offer comparable or superior x-ray detection efficiency to film-based detectors or x-ray cameras and thus reduce patient risk. Preferably the active detector area should be nearly 100% of the total detector area so that the carrier can be of a comparable size to the active x-ray detector. The dental x-ray detector would be sufficiently robust such that failure rates due to damage or exposure limits are small or negligible.

SUMMARY

The invention utilizes x-ray storage phosphor technology (including nanoparticle storage phosphor ceramic plates capable of extremely high spatial resolution) combined with amplified photodetectors to develop cost-effective detector systems for digital x-ray dentistry with imaging properties comparable or superior to existing analog x-ray film-screen units or digital x-ray cameras detector systems.

Although applications discussed herein are primarily directed at dental x-ray imaging, in principle the invention can also be used to detect charged particles (alphas, betas, protons, etc.) and neutrons (as well as other neutral particles) or mixed radiation fields (multiple radiation types at one or more energies). Thus, applications such as, but not limited to, radiation monitoring (for example, radiation film badges) can utilize versions of this invention.

One implementation of the invention provides flat or shaped small area storage phosphor plates of one or more sizes suitable for intraoral imaging of one or more teeth by exposure to x-rays. Unexposed small area storage phosphor plates (bare or framed) are each sealed in protective storage phosphor carriers (SP-carriers) comparable to the carriers used with x-ray film (light-tight, impenetrable-by-liquids, x-ray transmissive).

The SP-carrier, relative to the x-ray film carrier, offers comparable or easier positioning for the dentist and comparable or improved comfort levels for patients due to a reduction in size made possible by using the small area storage phosphor plate in place of film. The SP-carrier can incorporate a flap or frame that aids in maintaining the position of the detector in the patient's mouth (a feature frequently included for intraoral dental x-ray film carriers). The SP-carrier can include a bar code or number on the front or back side which can be scanned by a computer system or entered manually into a computer enabling identification with a particular patient. Alternatively, the SP-carrier or storage phosphor plate (or its protective frame) can incorporate an RFID which can be automatically identified with a specific patient when passed near an RFID reader. A small area storage phosphor plate can be removed from its SP-carrier by manual or automated mechanical means prior to readout of the small area storage phosphor plate by a suitable optical scanning beam mechanism.

An optional thin foil (or deposited layer) of an attenuating material (including alloys) such as copper, silver, lead, gold, etc. can be encapsulated and attached to, or incorporated into, the protective SP-carrier. This optional thin foil is located behind the small area storage phosphor plates (the front side of the storage phosphor plate is adjacent to the teeth) in order to provide additional radiation shielding for tissue and to reduce detected backscatter. An alternative option is to attach the thin foils to the small area storage phosphor plate or its frame (if present). Multiple small area storage phosphor plates of the same or different storage phosphor materials can be stacked (comprising a hybrid storage phosphor plate), held within a SP-carrier, and used in place of a single small area storage phosphor plate within a SP-carrier for dental x-ray imaging. Hybrid storage phosphor plate can be used to attain dose reduction, energy resolution and contrast enhancement. In addition diagnostic imaging applications that utilize multiple particle types (for example fast and slow neutrons, neutrons and photons, etc.) can also utilize hybrid storage phosphor plates.

Once a tooth or teeth are x-rayed the SP-carrier can be taken to a dark room or dimly-lit room where the exposed small area storage phosphor plate can be removed from the SP-carrier by manual means (such as by cutting the protective plastic, grasping the edges of the storage phosphor plate or its mounting frame, and pulling the storage phosphor plate from the SP-carrier) and loaded into the (light-tight) dental storage phosphor scanner device. Automated mechanical means of removing the SP-carrier can be integrated into the dental storage phosphor scanner device. Then the SP-carriers can be fed directly into the dental storage phosphor scanner device without the use of a dark room (saving space costs).

The dental storage phosphor scanner device has properties of both an analog dental film processor (designed for processing small area films) and a large area storage phosphor plate scanner processor used in x-ray radiology (which combines optical laser beam scanning with a translation stage) with the additional benefits of compact size and no required development chemicals. The dental storage phosphor scanner device identifies and scans the small area storage phosphor plate with a (pulsed or continuous) fine optical laser beam or LED beam or other suitable optical radiation source mechanism in order to discharge the storage phosphor plate pixel by pixel. Fluorescent light is detected by at least one amplified photodetector providing a digital readout.

Single beam, dual readout designs have been described in the literature (Rowlands J., Phys. Med. Biol. 47, pp. 123-166 (2002)). Single and dual readout versions of the dental storage phosphor scanner device benefit from the small scanning area compared to the large area storage phosphor plate scanner processor used in x-ray radiology. Scanning and light collection optics (lenses, fibers, mirrors) are simplified and efficiency improves because the scanning range is reduced and the photodetector can be positioned much closer to the storage phosphor plate versus (for example) a long fiber optic bundle that couples the entire width of a large storage phosphor plate to a much smaller PMT.

Commercial amplified 1-D and 2-D photodetectors such as PMTs, APDs, SiPMs, low-light and amplified CCDs, etc. can have sensitive surface areas that are (at least) a substantial fraction of the small area storage phosphor plates. A sufficiently large photodetector surface area allows one-to-one (or better) optical coupling or air coupling to be employed. Alternatively, scanning can be performed by scanning line by line within successive sub-regions of a small area storage phosphor plate and thereby maintain a favorable ratio between storage phosphor plate readout surface area and the photodetector surface area. This requires that a 2-D mechanical translation capability be incorporated into the scanner. Readout rates can be enhanced by implementing multiple scanning beams paired with multiple amplified photodetectors. Wavelength shifting (WLS) films may be applied to the storage phosphor plate directly or to the collecting optics coupled to the readout photodetector in order to provide an improved response for the readout photodetector.

Readout data can be processed by a computer within the dental storage phosphor scanner device or transferred and processed by an external computer. Images can be displayed electronically or printed. Each small area storage phosphor plate is tagged with a unique code or codes by one or more standard methods (printing, engraving, implantation of an RFID chip, etc.). Image processing algorithms can be applied (if required) to correct for position-dependent response variations in each small area storage phosphor plate using calibration data specific to each storage phosphor plate. Calibration data can be provided from the supplier or instructions can be provided enabling on-site calibration.

Next, additional image processing algorithms can be applied to the data in order to compensate for changes in exposure levels, changes in x-ray spectrums, corrections in display parameters, contrast enhancement, edge-sharpening, search operations, etc. After readout the small area storage phosphor plate can be fully-discharged and then reused on-site (if appropriate equipment is available to repackage the small area storage phosphor plate with a new SP-carrier) or returned to a processing center for inspection and repackaging. In either case the same operations need to be completed. The small area storage phosphor plate should be fully discharged.

The small area storage phosphor plate can be scanned or imaged for surface scratches and internal optical defects as a means of quality assurance. The last step is to seal the small area storage phosphor plate within a SP-carrier along with optional attenuating thin foils, ready for use in dental x-ray imaging. Any components that cannot be reused are stored for recycling. Tiling of small area storage phosphor plates (or hybrid storage phosphor plates) within a SP-carrier can be used to emulate a storage phosphor plate of larger area or a storage phosphor plate with a curved geometry. Single and tiled intermediate and large area storage phosphor plates are suitable for non-intraoral dental x-ray imaging.

The application of small area storage phosphor plates in dental x-ray imaging suggests that small area storage phosphor plates (and larger sizes) could be useful for other radiation detection applications such as radiation monitoring. In this application the carrier containing the radiation detector is typically referred to as a film-badge holder (even when the traditional film detector is replaced by other detector materials such as TLDs, OSLs, or charge storage detectors). Radiation exposure due to single or mixed radiation fields (at one or more energies) can be monitored. Multiple small area storage phosphor plates of the same or different storage phosphor materials can be stacked (comprising hybrid storage phosphor plates) and/or arranged in a tiled pattern within a SP-carrier comparable to a film-badge holder. Either nanoparticle storage phosphor ceramic plates or conventional storage phosphor plates can be employed since superb spatial resolution is not necessary in many cases.

These and other advantages of the present invention will become apparent upon reference to the accompanying drawings and the following description.

The details of one or more embodiments of the invention are set forth in the accompanying drawings and the description below. Other features, objects, and advantages of the invention will be apparent from the description and drawings, and from the claims.

All publications, patents, patent applications, U.S. Patent Office Disclosure Documents, cited herein are hereby expressly incorporated by reference for all purposes.

DETAILED DESCRIPTION

The invention provides a digital dental x-ray imaging system that combines the positive attributes of dental analog x-ray film-screen detectors and digital dental x-ray cameras by utilizing available, high resolution, storage phosphor plate technology in a small area format combined with amplified photodetectors that generate an electronic signals resulting in a digital readout. One cost advantage associated with the small area storage phosphor plate format is the expected increase in manufacturing yield of small area imaging plates compared to large area imaging plates required for applications such as x-ray mammography.

The invention provides cost-effective detector systems for digital x-ray dentistry with imaging properties comparable or superior to existing analog x-ray film-screen or digital x-ray cameras detector systems. Variations of this invention will be described that can be used for non-dental radiation detection applications (such as radiation monitoring with film badges and radiographic imaging) in order to detect specific types of radiation at one or more energies such as photons (x-rays, gamma rays), charged particles (alphas, betas, protons, etc.), neutrons (and other neutral particles), or mixed radiation fields (multiple radiation types) at one or more energies.

The invention provides flat or shaped small area storage phosphor plates of a rigid nature that are suitable for imaging one or more teeth with at least one x-ray exposure. In some cases a shaped plate (for example a curved plate) may be preferred over a flat plate since the shaped plate may be superior with respect to following the curvature of the mouth.

Figure 1:
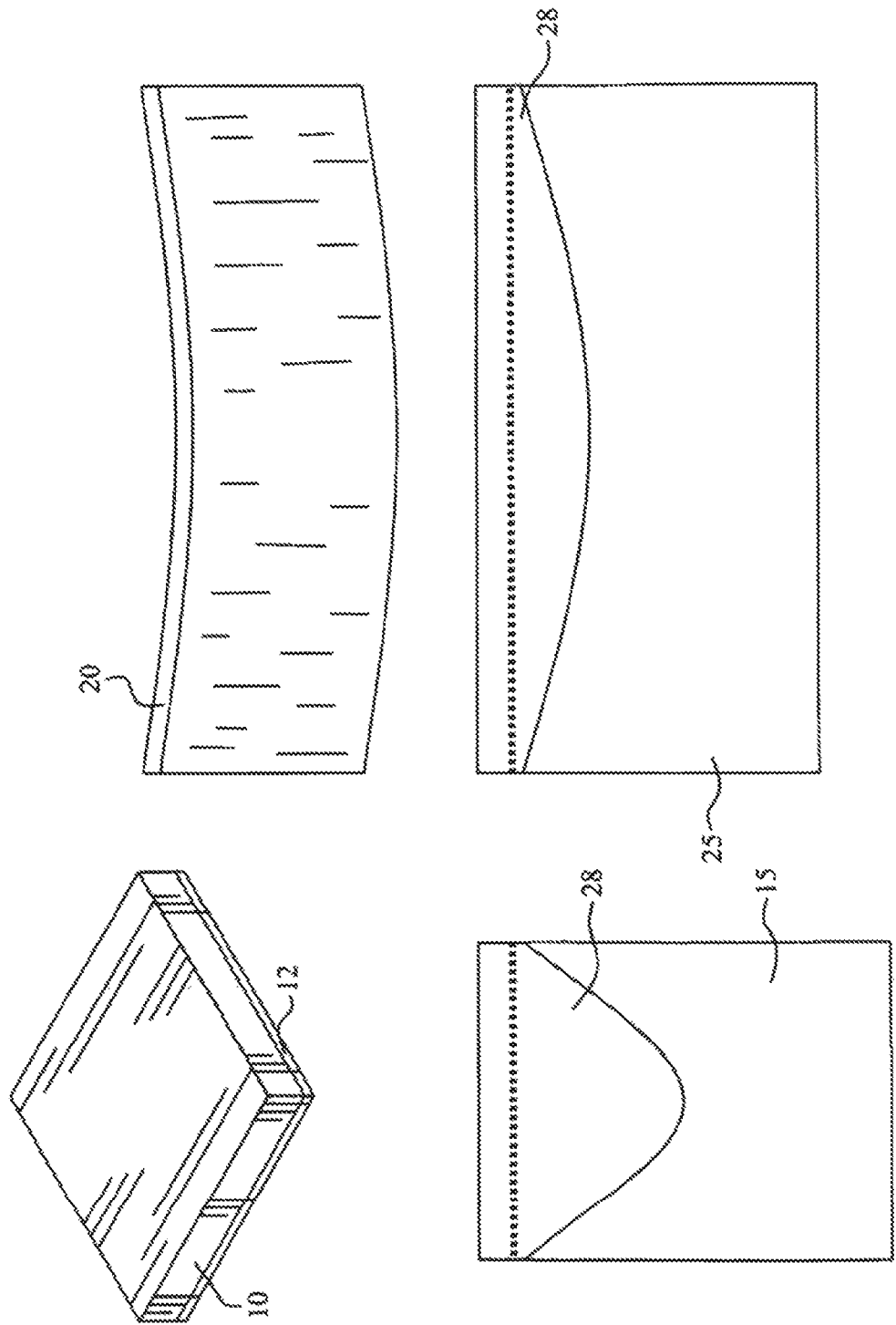
FIG. 1 illustrates a perspective view of flat and shaped small area storage phosphor plates with suitable SP-carriers.

FIG. 1 shows flat 10 and shaped 20 small area storage phosphor plates and suitable SP-carriers 15 and 25. The flat storage phosphor plate has an optional reflective coating 12 applied to one surface. The SP-carriers show a flap 28 for positioning inside the patient's mouth. Various types of thin protective layers (fixed or movable) can be included with these small area storage phosphor plates such as plastics, glass, fiber array plates and deposited films. The thickness of the small area storage phosphor plates and the choice of storage phosphor material can be (approximately) optimized in terms of spatial and contrast resolution as well as radiation exposure for the typical x-ray beam spectrum appropriate for an adult, teen, or child mouth. This optimization process, based on phantoms and typical x-ray beam spectra, is well-established in the field of x-ray radiology for analog x-ray film-screen detectors as well as x-ray storage phosphor and electronic detectors.

Image spatial resolution requirements may vary based on the subject. The optical scanning (readout) beam cross section can be adjusted in size from small area to large area by ordinary optical means so that the readout pixel size can be selected within a range of small area to large area pixels (fine to coarse spatial resolution). An advantage of imaging with large area pixels is a reduction in patient dose assuming that the loss in spatial resolution is acceptable. Sufficiently low readout noise per small area pixel permits large area pixels to be electronically synthesized by combining the readout signals from multiple small area pixels and thereby achieve patient dose reduction. This electronic pixel synthesis can be implemented in either the analog stage (extending the signal integration period) and/or the digital stage of data acquisition (combining uniform or elongated pixels during data processing).

Unexposed, fully-discharged small area storage phosphor plates are each sealed in a light-tight, impenetrable-to-fluids, protective SP-carrier made of a suitable materials widely used for conventional intraoral dental x-ray film carriers (such as x-ray transmissive plastics). Protective, light-tight, plastic carriers (which typically include a flap or frame that aids in positioning inside the mouth) are often employed with dental x-ray film-screen detectors. The SP-carrier can be removed by manual or automated mechanical means prior to readout by a suitable optical scanning beam mechanism. Optionally, the flat or shaped small area storage phosphor plate can be mounted in a small, light protective frame made of suitable strong, lightweight materials (plastics, ceramics, metals) for ease of handling and to ensure the structural integrity of the plate is maintained.

The small area storage phosphor plate and protective frame are encapsulated within the SP-carrier prior to use. Optically transmissive, scratch-resistant coatings can be applied to the surfaces of the small area storage phosphor plate. An optional thin foil (or deposited layer) of an attenuating material of appropriate effective atomic number and density (for example: copper, silver, lead, gold, alloys) can be incorporated with either the small area storage phosphor plate (or its protective frame if present) or the SP-carrier adjacent to the back side of the small area storage phosphor plates (the front side is adjacent to the teeth) in order to provide additional radiation shielding for tissue and to reduce detected backscatter. The small area storage phosphor plate detector (and its protective frame if present) and SP-carrier can therefore function as a direct replacement for the analog x-ray film-screen detector and carrier widely employed for intraoral dental x-ray imaging.

If the storage phosphor plate is fragile or exposed to excessive wear a movable front protective layer may be combined with a protective frame to form a protective cage that surrounds the storage phosphor plate. A movable front protective layer (a protective cap or cover or shell) can be made optically opaque in order to shield a storage phosphor plate from room light or other sources of light that could unintentionally discharge the exposed storage phosphor plate. A movable front protective layer that shields the readout surface (which is also typically the x-ray beam entrance surface) of the storage phosphor plate from physical damage should be relatively transparent to x-rays over the imaging region of interest (which implies a uniform thickness over the area of the storage phosphor plate that is used for imaging).

Optionally one or more calibration strips can be incorporated along one or more edges of the region of the movable front protective layer that will be imaged, providing quality control capability and/or dosimetry estimate capability during readout of the exposed storage phosphor plate. In addition to preventing direct physical contact with the storage phosphor plate the movable front protective layer reduces the probability that dust can deposit on the storage phosphor plate and interfere with optical scanning. (This reduces the requirements on any blowers, sprays or electrostatic devices employed in the readout unit to remove dust from the surface of the storage phosphor plate.)

In one implementation a storage phosphor plate with a protective frame is inserted into a movable front protective layer in the shape of a rectangular cap (or cover or shell), which together comprise a protective cage. The rectangular cap can have a half open face (the base of the storage phosphor plate or frame comprises the other face which completes the cap) or be fully enclosed except for either one open end or both open ends (similar to a match box that slides into a rectangular matchbox cover or shell). After the storage phosphor plate and protective frame are inserted into the movable front protective layer cap the resulting protective cage can be placed within the SP-carrier and the SP-carrier can be sealed.

Figure 4:
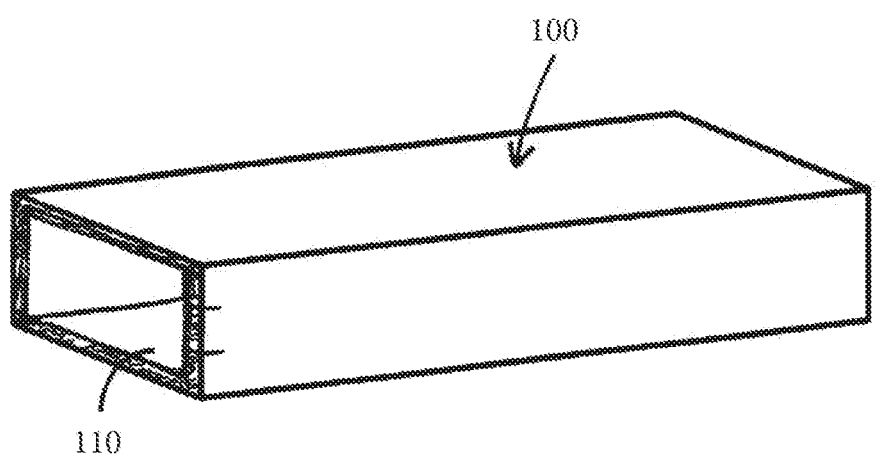
FIG. 4 illustrates a perspective view of a movable protective layer or cap incorporated into an SP-carrier, permitting insertion of a storage phosphor plate and its protective frame.

FIG. 4 shows a rectangular cap or shell 100 with one open end 110 into which a storage phosphor plate and its protective frame can be inserted and later extracted after x-ray exposure for optical scanning. In another implementation a movable front protective layer can be attached to a protective frame that surrounds the storage phosphor plate. It can snap onto or snap into, slide into or slide onto the protective frame.

Figure 5:
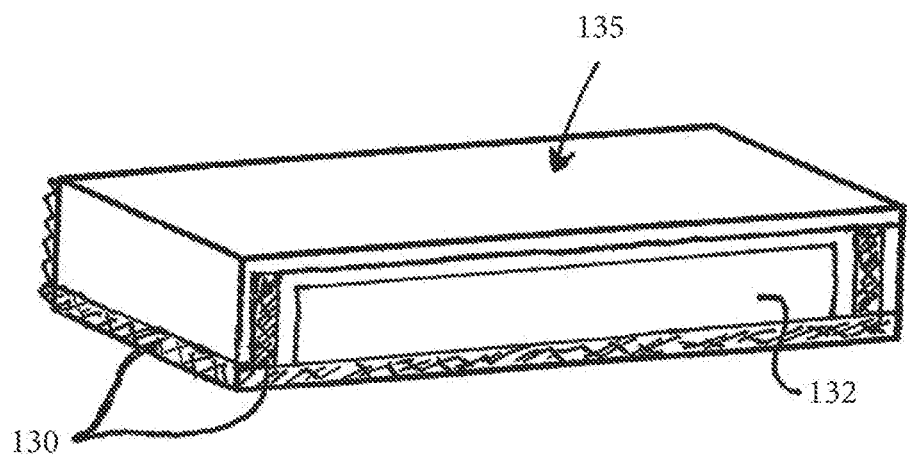
FIG. 5 illustrates a perspective view of a movable protective layer that can slide onto the protective frame of a storage phosphor plate.

FIG. 5 shows a transparent edge-on view of a storage phosphor plate 132 attached to a protective frame 130 with a movable front protective layer 135 that slides onto the protective frame. In another implementation the movable front protective layer in the shape of a previously described rectangular cap or cover or shell, as shown in FIG. 4 and FIG. 5, is integrated with the SP-carrier into which a storage phosphor plate with protective frame is inserted, comprising a protective cage. In another implementation a movable front protective layer such as a cover can be attached by a hinge mechanism or a pivot device (such as a screw) to the protective frame that permits the movable front protective layer to be rotated out of the optical scanning beam path.

Figure 6:
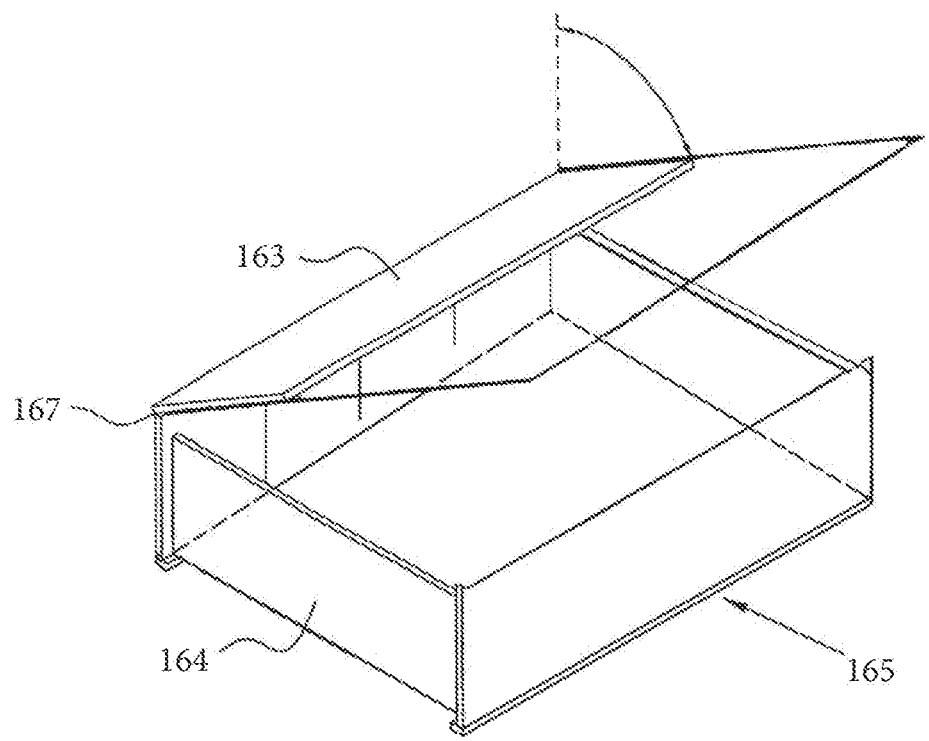
FIG. 6 illustrates a perspective view of a movable protective layer that is attached to the protective frame of a storage phosphor plate by a hinge mechanism.

FIG. 6 shows a protective frame with a base 185, sidewalls 164 and a rotatable movable front protective layer or cover 163 attached by a hinge 167 to the protective frame.

One or more dimples (small bumps) or functionally-equivalent markers can be included near the edge of the movable front protective layer to indicate that the movable front surface of the storage phosphor plate is facing the x-ray source (a technique already used with dental film-based detectors).

Alternatively one or more dimples or functionally-equivalent markers can be incorporated into the protective frame in order to establish which surface should face the x-ray source. The frame can also have an asymmetric shape so that it can only fit into the SP-carrier in the correct orientation in which the front face of the SP-carrier (the x-ray side) is adjacent to the front face of the storage phosphor plate. It should be understood that the movable front protective layer is typically made from strong, lightweight materials such as plastics (with scratch-resistant coatings if needed) which are x-ray transmissive and can be made optically opaque. Edges of the movable front protective layer or protective frame can be beveled or rounded in order to mitigate issues concerning patient discomfort.

Once a tooth or teeth are x-rayed the exposed small area storage phosphor plate (including any protective frame and movable front protective layer) and SP-carrier unit can be fed into the (light-tight) dental storage phosphor scanner device which has properties of both an analog dental film processor and a large area storage phosphor plate scanner used in x-ray radiology. The SP-carrier can be removed manually in a dark room (or dimly-lit room) and loaded into the dental storage phosphor scanner device. Automated mechanical means of removing the SP-carrier can be integrated into the dental storage phosphor scanner device. Then SP-carriers can be fed directly into the dental storage phosphor scanner device, eliminating the cost associated with a dedicated dark room (or a dimly-lit room).

If the storage phosphor plate is encapsulated within an optically opaque protective cage comprised of a protective frame and movable front protective layer, then the SP-carrier can be separated from the protective cage under normal room lighting and the encapsulated storage phosphor plate can be fed into the scanner device where the movable front protective layer is mechanically separated from the protective frame. In another implementation the movable front protective layer can be separated manually from the protective frame under dim light and then fed into the scanner.

The loaded small area storage phosphor plate is secured and then scanned (readout) with a (pulsed or continuous) fine beam provided by an optical laser, LED, or suitable optical discharge mechanism in order to cause the storage phosphor plate to fluoresce, pixel by pixel. A fraction of the fluorescent signal from each pixel is collected and transported to an amplified optical sensor. The amplified optical sensor converts the fluorescent signal into a raw electronic signal that is digitized, processed, and stored as the raw digital readout by a computer (either internal or external to the dental storage phosphor scanner device) where additional processing can be employed.

Possible optical (readout) sensors include, but are not limited to, photoemissive detectors such as photomultiplier tubes and proximity tubes as well as amplified semiconductor devices that include, but are not limited to, silicon-based detectors such as electron multiplying CCDs (EMCCDs), Geiger-mode silicon photomultiplier (SiPM) arrays or elements, internal discrete amplification detector (iDAD) arrays or elements, avalanche photodiode (APD) arrays or elements, position-sensitive APDs (PSAPDs), etc. Well-known semiconductor detector materials other than silicon can be employed if they are cost-effective (for example, offering reduced temperature control-cooling costs or gain or a poor response to the scanning beam wavelength).

Since the active area of these storage phosphor plates is small, the surface geometry of the readout sensor(s) can be optimized for a particular scanning format. A readout sensor with a linear cross section can be used with a line scan geometry in which the sensor remains aligned with the scanning beam. A readout sensor with an area cross section comparable to that of the storage phosphor plate can be used with a line scan geometry or an area scan geometry (in which the entire storage phosphor plate is illuminated at once or a sequence of sub-regions is illuminated until the entire storage phosphor plate has been scanned). Thus, there is a degree of flexibility as to the choice of readout sensor format (single element, 1-D array and 2-D array readout detectors). The long fiber bundles used to couple a small area readout sensor to a large area phosphor plate can be greatly reduced in length, replaced by mirror collected optics or eliminated altogether (reducing optical losses while making the dental storage phosphor scanner device more compact).

Appropriate optical filtration is used to eliminate any undesirable scanning beam optical radiation from reaching the optical readout sensor. Versions of the automated dental storage phosphor scanner device can be implemented such that one or multiple small area storage phosphor plates can be scanned simultaneously based on workload requirements. Once fully discharged the small area storage phosphor plate can then be repackaged in a new SP-carrier along with optional attenuating thin foils on-site (if suitable equipment is present) or shipped off-site to a commercial processing center for repackaging. In either case several procedures should be performed prior to reuse of the small area storage phosphor plate for dental x-ray imaging. The small area storage phosphor plate should be fully discharged and the integrity of the storage phosphor plate should be evaluated for surface scratches and internal defects as a means of quality assurance. Any components that cannot be reused are stored for recycling or returned to the manufacturer.

The cost of owning the dental storage phosphor scanning device for dental x-ray imaging should be significantly reduced compared to existing commercial, clinical large area storage phosphor plate scanning (readout) units from vendors such as KODAK since space requirements and scanner component costs should be reduced (the scanning process only needs to cover a small area and workload demands are likely to be reduced relative to the large scanners used in hospitals).

Preferably each small area storage phosphor plate (or its frame) is tagged with a unique code or codes by one or more standard methods (printing, engraving, implantation of an RFID chip, etc.) which are identified during the readout process. Using calibration data specific to each small area storage phosphor plate then image processing algorithms can be applied (if required) to the stored raw digital readout signals in order to correct for position-dependent response variations in each small area storage phosphor plate. Calibration data can be provided from the supplier or instructions can be provided to the end user enabling on-site calibration.

Next, additional image processing algorithms can be applied by the computer and/or by a separate computer attached to a display for purposes of modifying the raw data in order to compensate for changes in typical exposure levels and storage phosphor energy-dependent response, provide multiple energy imaging (if applicable), patient dose reduction, as well as to provide corrections in display parameters, contrast enhancement, edge-sharpening, search operations, etc.

Appropriate conversion and/or transmission coatings can be applied to the readout surface of a storage phosphor plate in order to increase the readout signal. Appropriate conversion and/or reflective coatings can be applied to the surface opposite the readout surface of a storage phosphor plate in order to increase the readout signal. Absorptive coatings for the optical scanning beam can be employed as needed. Both surfaces (front and back faces) of a storage phosphor plate can be read out in which case conversion and/or transmission coatings can be applied to both surfaces in order to increase the readout signal.

Preferably the reflective coatings are efficient at reflecting optical fluoresce radiation from the storage phosphors. In one implementation the reflective coating or coatings is/are at least semi-transparent to the optical scanning beam radiation. In one implementation the reflective coating or coatings is/are absorptive to the optical scanning beam radiation. Transmissive, reflective, absorptive and conversion coatings can include (but are not limited to) single films, multi-layers films, retroreflective films, nanostructures, photonic band gap structures, and WLS materials (as described in Nelson, U.S. patent application Ser. No. 12/384,459, and incorporated herein).

Structured storage phosphor plates can be used to improve fluorescent signal collection by reducing optical trapping and in some cases spatial resolution. Structured storage phosphor plates can be formed by milling (by various well-known means such as laser or ion beams) a 2-D array of small holes into the storage phosphor plate and there by create an internal scattering structure. Structured storage phosphor plates can be formed from storage phosphor fibers (grown in columnar geometry or manufactured from storage phosphor fiber bundles). A reflective coating can be applied to the non-readout surface.

Nanoparticle storage phosphor ceramic glass material can be pulled through a die to form storage phosphor fibers that can be combined to form storage phosphor fiber arrays. (In a similar manner a conventional scintillator or nanoparticle glass ceramic scintillator material can be pulled through a die to form scintillator fibers that can be combined to form scintillator fiber arrays.)

These scintillator fiber arrays can be attached to an optically sensitive high resolution readout digital camera such as an amplified (providing gain greater than 1.0) or unamplified semiconductor digital camera, including but not limited to, CCD or CMOS digital cameras. The scintillator fiber arrays are used directly in place of a very thin scintillator screen deposited on top of a fiber optic coupler. Stopping power could increase noticeably while maintaining reasonable optical coupling efficiency with very high spatial resolution. A reflective coating can be applied to the x-ray beam entrance surface of the scintillator fiber array.

Optionally, the small area storage phosphor plates can be manufactured as a structured 2-D array (Nelson, U.S. Pat. No. 5,258,145). Alternatively, the front surface and/or the readout surface of the small area storage phosphor plates can be structured by cutting, etching, casting, etc. (Nelson, U.S. Pat. No. 5,017,782). Reflective and/or conversion coatings can be combined with structured small area storage phosphor plates. Preferably these reflective and/or conversion coatings are absorptive at the wavelengths of the optical scanning beam so as to improve spatial resolution. If an absorptive layer or coating is present beneath the reflective and/or conversion coating then the coating can be at least semi-transparent to the optical scanning beam radiation.

If the back surface of the storage phosphor plate is appropriately structured then readout spatial resolution can be improved by filling the voids within the structure with either an absorptive material of the optical beam or a reflective (or conversion) material of the fluorescence signal but absorptive of the optical scanning beam. The structures create optical channels with absorptive walls for the scanning beam. Furthermore, if a coating or substrate of comparable or higher index of refraction than the storage phosphor is present at the back surface then this coating or substrate can be structured and coated in order to enhance spatial resolution. The coating or substrate material itself may be absorptive of the optical scanning beam. One option is to structure the front surface of the substrate, apply appropriate films as desired to enable at least one of reflection, conversion and absorption. Next deposit the storage phosphor material on the patterned substrate. A potential benefit is that the storage phosphor material may mimic the patterned substrate as it grows (resulting in a structured storage phosphor plate).

Figure 2:
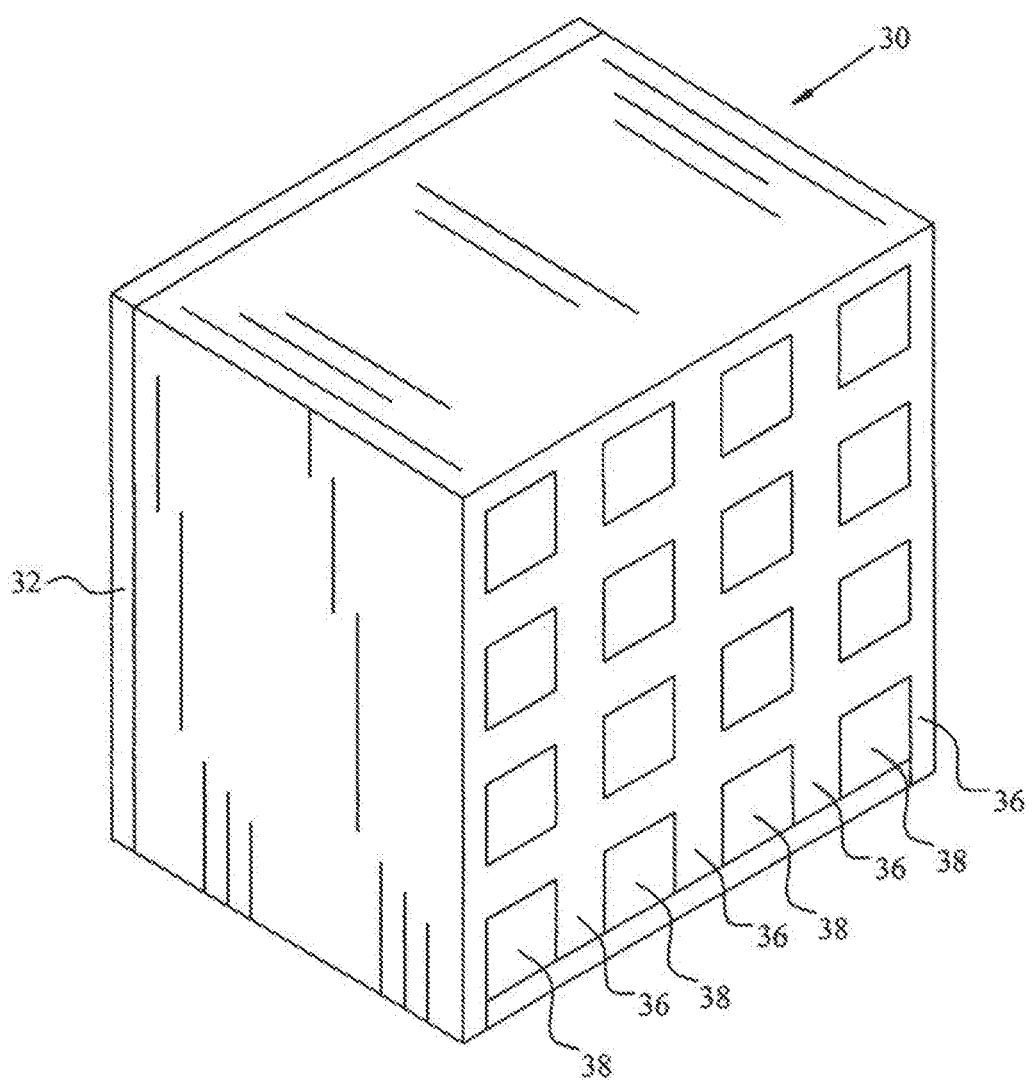
FIG. 2 illustrates a structured storage phosphor plate.

FIG. 2 show a view of a structured storage phosphor plate 30 with reflectively coated storage phosphor detector channels 38 (pixels) with reflective surfaces 36. An optional reflective coating 32 may be applied to one surface. Pixel sizes are exaggerated for clarity (an actual structured storage phosphor plate would contain at least as many pixels as a digital x-ray camera of comparable active detector area). Additional techniques can be employed to reduce optical trapping and thereby enhance fluorescent light extraction.

Figure 7:
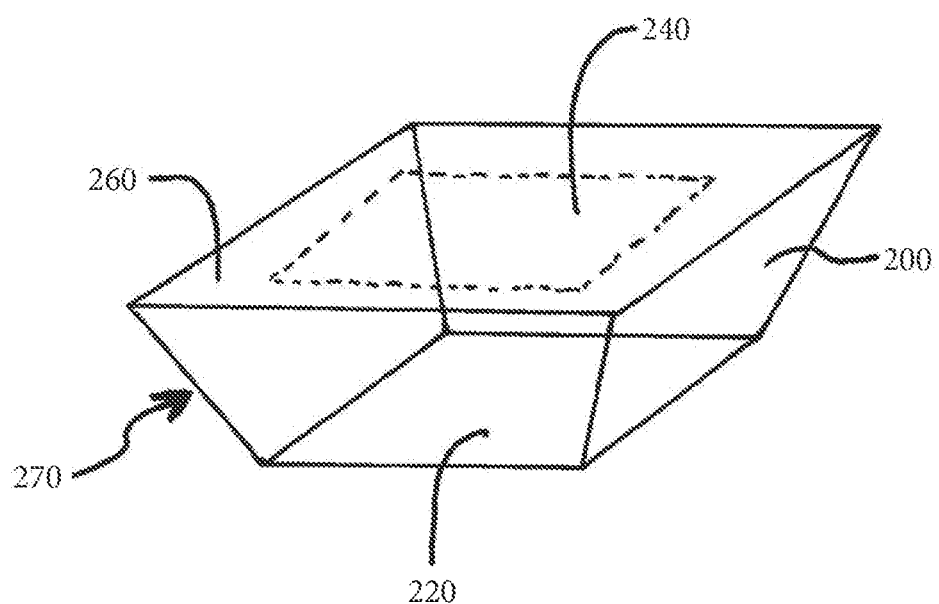
FIG. 7 illustrates a perspective view of a storage phosphor plate with a beveled edge

FIG. 7 shows a storage phosphor plate 270 with an extended x-ray beam entrance surface 260 larger than the base surface 220. The beveled edges 200 of the storage phosphor plate reduce light trapping within storage phosphor. Reflective coatings of various designs (specular, diffuse, low-index, multilayer, wavelength-shifting or combinations thereof) can be added to the surfaces of the beveled edges. Other types of beveled edge geometries, including curved or patterned shapes, can be implemented.

Optical scanning is limited to a region 240 smaller than the area of the base so as to avoid the direct optical scan beam from interacting with the beveled edge. Note that a beveled edge structure may be or may not be integral to the storage phosphor plate. A non-integral beveled edge structure can be attached or coupled to a storage phosphor plate through a variety of means (deposition, adhesive, tension) and can be comprised of non-storage phosphor plate materials. An integral beveled edge structure can be treated by radiation or heat to reduce its fluorescence properties as needed.

Figure 8:
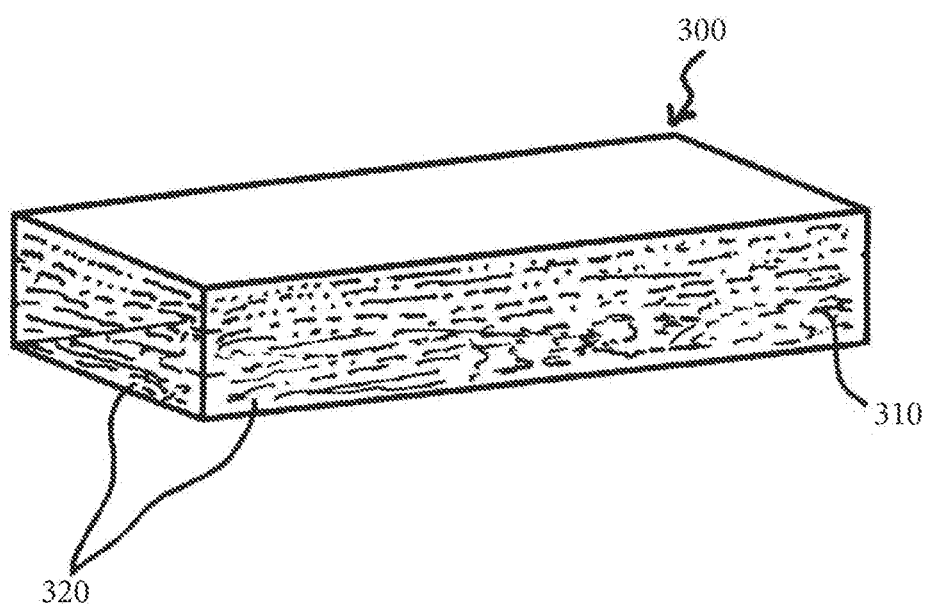
FIG. 8 illustrates a perspective view of a storage phosphor plate with a straight edge and a diffuse reflective coating.

In another implementation, FIG. 8 shows a simple diffuse or wavelength-shifting reflective coating 310 applied to the conventional straight edge side walls 320 of a storage phosphor plate 300. In yet another implementation a 2-D array of small holes can be milled by various means (such as laser or ion beams) into the storage phosphor plate and there by create an internal scattering structure.

Multiple small area storage phosphor plates of the same or different storage phosphor materials can be stacked (comprising hybrid storage phosphor plates) and held in a SP-carrier. Tiling of small area storage phosphor plates (or hybrid storage phosphor plates) within a SP-carrier can be used to emulate a storage phosphor plate of larger area or a storage phosphor plate with a curved geometry. A hybrid, small area storage phosphor plate that can be used for purposes such as dose reduction, multiple energy imaging and contrast enhancement combines two or more small area storage phosphor plates back-to-back. The small area storage phosphor plates may be comprised of different storage phosphor materials, thicknesses, coatings and surface structures.

Consider the specific implementation of stacked, dual small area storage phosphor plates. One or more sheets of material can optionally be positioned in between the two storage phosphor plates. These sheets can serve one or more functions; optically-isolating the plates, acting as a reflective surface, filtering x-rays. A single or dual scanning readout system can be employed (Nelson, U.S. Pat. No. 4,937,453). The two small area storage phosphor plates can be structured and they can use reflective and conversion coatings.

Figure 3:
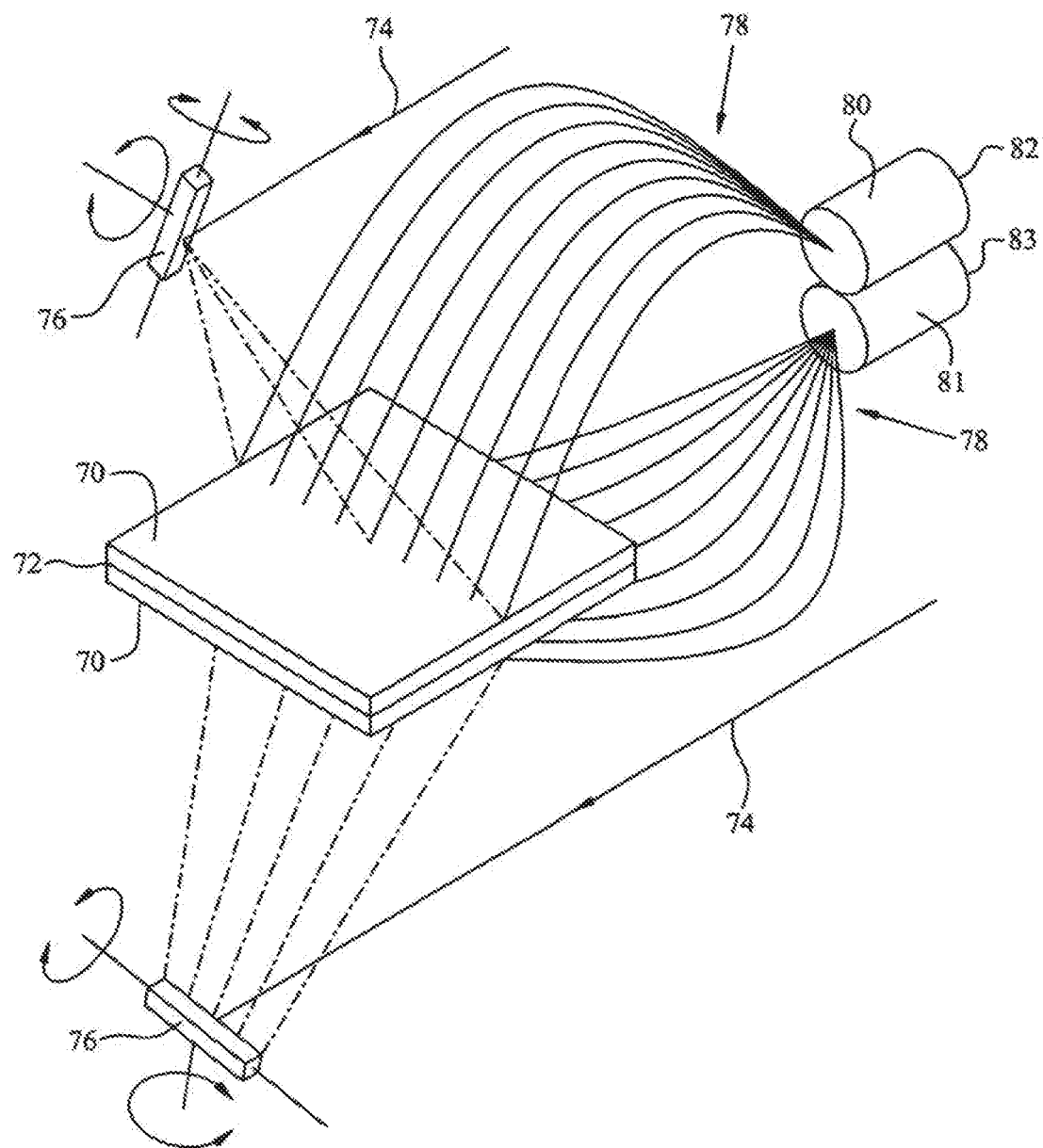
FIG. 3 illustrates a perspective view of a hybrid, flat, small area storage phosphor plate being scanned with an electronic link to a computer.

FIG. 3 shows a hybrid storage phosphor plate comprised of two storage phosphor plates 70, 71 with an intermediate sheet 72. Optical beams 74 (for example laser beams) of appropriate wavelengths for the corresponding phosphor plates are reflected from scanning mirrors 76 to the storage phosphor plates 70, 71 and fluorescent signals from the de-excited storage phosphors are coupled via light guides 78 to amplified photodetectors such as PMTs 80, 81 which generate output signals 82, 83 that are transferred to signal processing electronics and stored on a computer. Note that this configuration of a dual readout optical scanner can also be used with a single unstructured or structured small area storage phosphor plate by combining the two output signals prior to or after digitization. Implementing separable small area storage phosphor plates removes the requirement for optically-reflective or optically-absorptive layers or coatings between the small area storage phosphor plates. X-ray filtering layers can be employed as needed.

Numerous mounting formats can be implemented to permit multiple small area storage phosphor plates to be assembled into a rigid geometry and then separated after x-ray exposure during the readout phase. For example the small area storage phosphor plates can be mounted in a frame which allows the small area storage phosphor plates to snap together, be hinged together (similar to pages in a book), slide parallel to one another (such as a multi-level tray system), etc. Tiling of small area storage phosphor plates (or hybrid storage phosphor plates) within a SP-carrier can be used to emulate a storage phosphor plate of larger area or a storage phosphor plate with a curved geometry.

The use of storage phosphor plate technology in dentistry is not limited to intraoral sensors. Intermediate (moderate) area storage phosphor plates, ranging from approximately 4×4 cm$^2$ to 8×8 cm$^2$ (and even larger), are required for x-ray imaging applications such as implant placement and surgery, root canal therapy, extractions, etc. by periodontists, endodontists and orthodontists. The features described for small area storage phosphor plates and hybrid, small area storage phosphor plates (including tiling) can be replicated for intermediate area storage phosphor plates appropriate for these applications. A cost benefit can still be expected due to improved manufacturing yields relative to large area storage phosphor plates.

An optional anti-scatter x-ray grid can be employed between the patient and the intermediate area storage phosphor plate or the hybrid intermediate area storage phosphor plate. The dental storage phosphor optical scanning device described for use with small area and hybrid, small area storage phosphor plates is suitable for reading out intermediate area storage phosphor plates. Optical scanning can be performed line by line (employing 1-D translation) or scanning can be performed by scanning line by line within successive sub-regions of an intermediate area storage phosphor plate (a technique that can also be used with small area storage phosphor plates or large storage phosphor plates), and thereby maintain a favorable ratio between storage phosphor plate readout surface area and the photodetector surface area.

This sub-region optical scanning requires that 2-D mechanical translation capability be incorporated into the scanner. Alternatively an intermediate area or hybrid intermediate area storage phosphor plate of appropriate dimensions can be integrated with a dental storage phosphor optical scanning device to comprise an (integrated) dental storage phosphor imaging unit. The intermediate area or hybrid intermediate area storage phosphor plate would remain in the dental storage phosphor imaging unit. Raw image data can be transferred to an external computer for processing or the raw data can be processed within the dental storage phosphor imaging unit and then both sets of data can be transferred by a conventional means (wired, wireless, memory stick, etc.) to local computers (including displays with appropriate connectivity) or external computers for long term storage, processing and analysis and display. Images can be displayed electronically or printed. Optionally an image can be displayed on a small screen incorporated into the dental storage phosphor imaging unit.

Although the small and intermediate area storage phosphor plate detector technology is suitable for a many applications in dental x-ray imaging there are applications such as panoramic dental x-ray imaging that require large area storage phosphor plates. The features described for small area storage phosphor plates and hybrid small area storage phosphor plates, including tiling, can be employed for large area storage phosphor plates. The dental storage phosphor scanning device described for use with small area and hybrid small area storage phosphor plates can be expanded to read large area (flat or curved) storage phosphor plates.

A variation of the dental storage phosphor imaging unit described for an intermediate area or hybrid intermediate area storage phosphor plate can be implemented by integrating a large area or hybrid large area storage phosphor plate of appropriate dimensions with a dental storage phosphor optical scanning device to comprise a larger dental storage phosphor imaging unit. The large area or hybrid large area storage phosphor plate would remain in the dental storage phosphor imaging unit that replaces panoramic x-ray film devices and digital scanners (that use, for example, a slit/slot scanning TDI-CCD detector systems). A similar design can be employed for intermediate area and large area general purpose and specific purpose diagnostic x-ray imaging applications such as mammography, chest imaging, etc.

An additional advantage of the storage phosphor plate technology is that a panoramic dental x-ray image can be acquired with a single short x-ray exposure or with a slit/slot scan format (such as employed with single or multiple slit/slot scanning film-screen, linear array or TDI-CCD detector systems). Preferably the optical scanning device will be translated with respect to the large area or hybrid large area storage phosphor plate. Variations in x-ray tube output during a scan can be monitored, stored, and used to correct the spatially-correlated readout signals from the large area or hybrid large area storage phosphor plate.

X-ray scatter reduction mechanisms include slit collimators, slot collimators and x-ray grids. Slit/slot scan systems offer inherent x-ray scatter reduction by means of a slit and slot x-ray collimators which create narrow beams. Single and multiple slit/slot collimators can be used with large area storage phosphor plates for applications such as x-ray mammography, chest radiography and general radiographic imaging (both medical and industrial). For the single short x-ray exposure format a focused anti-scatter x-ray grid can be employed between the patient and the large area or hybrid large area storage phosphor plate.

Sufficiently long-lived metastable excited states of particular storage phosphors allow these storage phosphors to be used for applications in radiation monitoring on a daily basis or longer. Various implementations of one or more small area storage phosphor plates (up to intermediate area storage phosphor plates) within a light-tight SP-carrier can be employed for radiation monitoring such as personnel film badges. Similar units (including up to large area storage phosphor plates) can be mounted at specific locations (often referred to as area monitoring) with respect to known or potential radiation sources.

The small area storage phosphor plates can be read out by a simple (light-tight) external reader that mechanically opens the SP-carrier, optically scans (in pulsed or continuous mode) and then fully-discharges the storage phosphor plate (or plates). The fluorescent signals are converted into raw digital signals that can be stored and then modified after applying corrective algorithms that correct the data based on the assumed types of particles, energy spectra and intensities, enabling dosimetry. Although external readers similar to a dental storage phosphor scanner device can be employed, in many cases the external reader can be simplified since a pixel is typically defined by either an entire storage phosphor plate or a relatively large sub-region of a storage phosphor plate (high speed, fine optical laser beam or LED beam scanning is typically not necessary).

A single small PMT, a SiPM (or other amplified optical detector), with appropriate optical coupling and spectral filtering may be employed as a photodetector. Alternatively the storage phosphor plates can be read out by incorporating the components of the simple external reader directly into the SP-carrier (an electronic SP-carrier). Within the electronic SP-carrier the storage phosphor plate (or plates) or sections thereof are illuminated by an optical LED or laser beam and a fraction of the fluorescence signal is optically coupled to an amplified photodetector. Various methods of optical coupling include, but are not limited to, direct coupling (one-to-one), lenses, mirrors and minifying light pipes.

The raw digital data and/or corrected data can be stored in the electronic SP-carrier and/or broadcast to a receiver (local or remote) for storage and retrieval and additional processing if desired. The electronic SP-carrier can be read out periodically (for example, at the end of a work shift or a radiological procedure, once every hour/day/week, etc.) or on-demand. Potentially the shorter the period of time the storage phosphor must integrate the radiation exposure the greater the range of possible storage phosphor materials that can be employed.

Specifically, the small area storage phosphor plate or plates can be utilized in a film-badge format appropriate for one or more radiation types and energy levels. Previously film-badge technology employed radiation detectors such as film, TLDs, OSLs, gels, chemicals, charged detectors, etc. which frequently included overlays with suitable pieces of filter materials to record single or mixed radiation fields at one or more energies (Turner, pp. 274-296).

A single small area storage phosphor plate or multiple small area storage phosphor plates (as well as hybrid storage phosphor plates and tiled single or hybrid storage phosphor plates) can be combined with appropriate filters in a light-tight SP-carrier or the filters can be integrated into a separate filter sheet that can be positioned adjacent to or attached to the SP-carrier in order to measure single or mixed radiation fields at one or more energies. Individual filter pieces (for example squares, rectangles, circles, annuli) can be arranged in arrays or patterns as is common in conventional film badge use. Filter materials such as plastic, lithium, boron, aluminum, iron, cadmium, lead, gold, uranium, etc. can be used to alter the energy and/or particle spectrum of incident radiation or act as secondary sources of radiation. When a separate filter sheet is employed it will preferably have a specific geometry that permits it to be attached to the SP-carrier only in the correct orientation so that filter pieces are positioned appropriately with respect to the storage phosphor plate. Mechanical slide or snap mounting are well-known means of attachment. Direct attachment can also be employed if desired.

Individual storage phosphor plates may contain a single storage phosphor type or a mixture of multiple storage phosphor types. In some cases a particular storage phosphor type may not require a filter due to its composition (for example, incorporating atoms with either low or high cross section for thermal/fast neutrons or low/high energy x-rays). Analyzing the output from a mixed storage phosphor may require the use of spectrum separation techniques in order to determine which of the phosphors has interacted with a specific type and/or energy of radiation. A mixed storage phosphor that requires different maximum optical wavelengths to transition from metastable states can be discharged in order, starting with the longest optical wavelength first.

Although the technique of using appropriate mixed storage phosphors to evaluate single or mixed radiation fields (particle type and/or energy) has been described for radiation monitoring applications it is straightforward to extend this technique to the small area storage phosphor plates detectors proposed for dental x-ray imaging and to large area storage phosphor plates that can be used for general x-ray radiology applications such as pediatric x-rays, x-ray mammography, chest x-rays, etc. This would provide an additional degree of energy-dependent information that could be used to improve image contrast and patient diagnosis. Energy-dependent information can also be obtained for small area or large area imaging with appropriate mixed storage phosphor plate detectors and multi-energy neutron radiation (for example, a spectrum with thermal and fast neutrons or a neutron energy continuum).

Small area storage phosphor plates (and any intermediate or large area storage phosphor plates) described herein, whether used for imaging or radiation monitoring, will optionally include tagging as an identification means that would be evaluated during the scanning process and be included in the readout data for purposes of quality control and tracking.

Variations on this small area storage phosphor plate detector invention for dental x-ray imaging include high resolution charged x-ray detectors where the level of discharge is related to the type and energy of the detected radiation. This should be differentiated from the Pockels readout optical memory (PROM) technology developed in the 1970s. PROM technology (based on charged, photoconductive and optically active sillenite crystals such as BGO, BTO, and BSO) can be used to detect x-rays. A polarized optical beam illuminates the exposed crystal which is read-out by a photodetector thereby providing a measure of the level of induced birefringence due to the ionizing radiation.

Figure 9A:
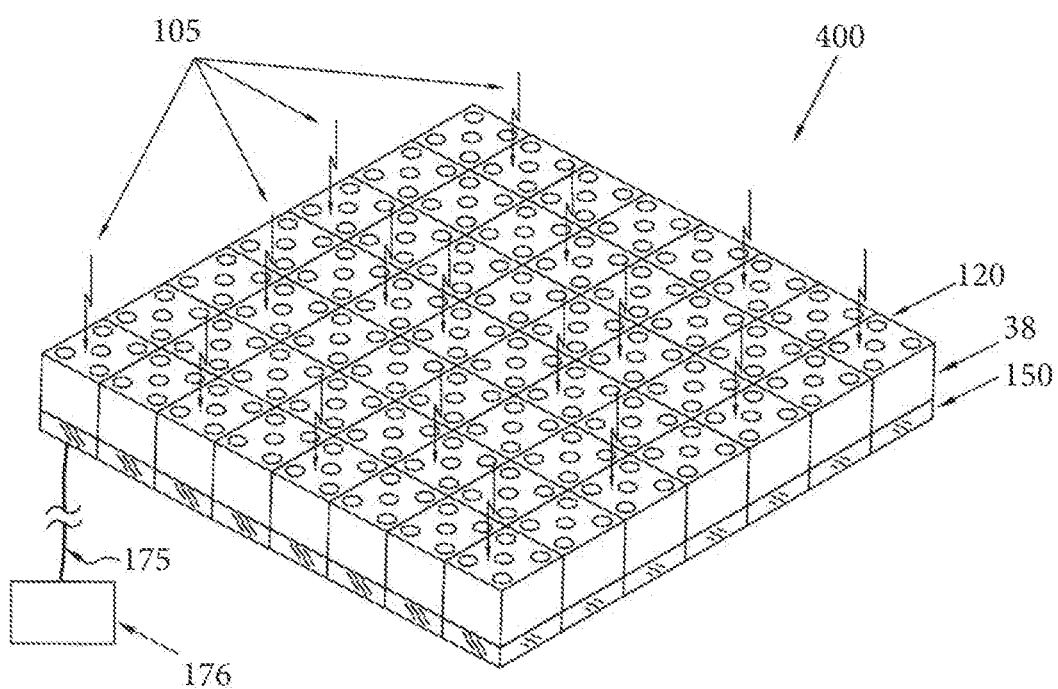
FIG. 9A illustrates a perspective view of a 2D semiconductor conductive mold x-ray detector with an array of holes that is electronically-coupled to an attached substrate incorporating readout circuitry with a power and communication link for connection to a computer.

The components of a digital x-ray camera for intraoral dental imaging are shown in FIGS. 9A-9D. FIG. 9A illustrates a perspective view of a (structured) semiconductor conductive mold x-ray detector 400 (a conductive mold semiconductor detector) with an array of holes 120 that are electronically-coupled to an attached substrate incorporating readout circuitry 150 with a power and communication link 175 for connection to a computer 176, with incident radiation field 105.

Figure 9B:
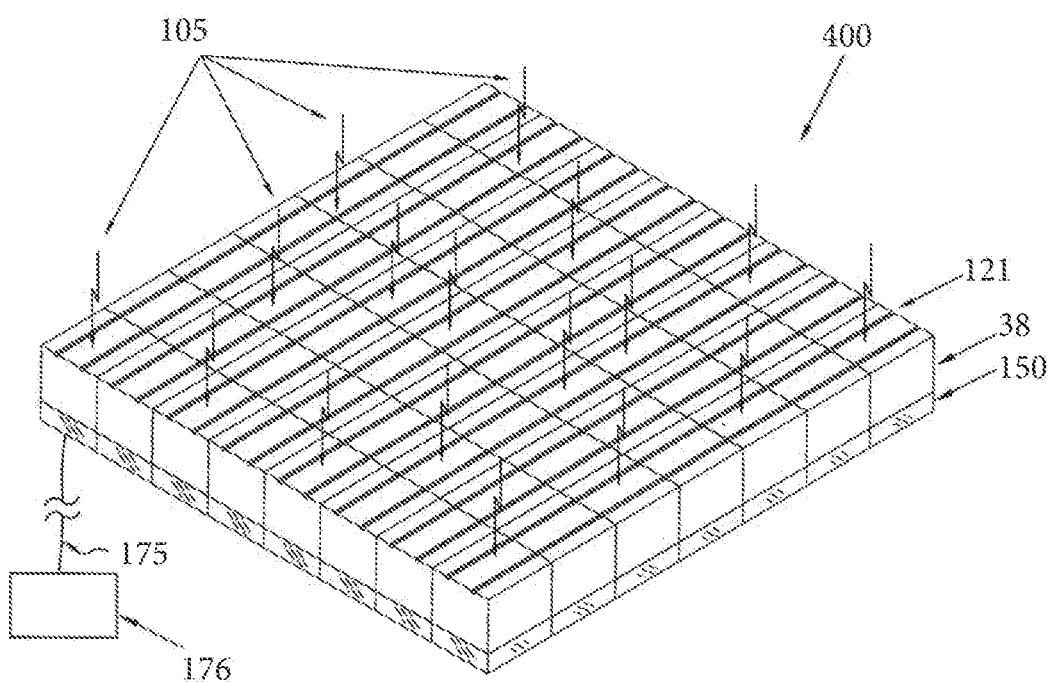
FIG. 9B illustrates a perspective view of a 2D semiconductor conductive mold x-ray detector with an array of channels that is electronically-coupled to an attached substrate incorporating readout circuitry with a power and communication link for connection a computer.

FIG. 9B illustrates a perspective view of a (structured) semiconductor conductive mold x-ray detector 400 with an array of channels 121 that are electronically-coupled to an attached substrate incorporating readout circuitry 150 with a power and communication link 175 for connection to a computer 176, with incident radiation field 105. The hole dimensions and channel dimensions as well as the number of holes and channels shown are for illustrative purposes only. Suitable semiconductor-based materials (nano-particles including Q-dots, polycrystalline or amorphous semiconductor materials) can be used to fill the holes or channels of the semiconductor conductive mold. Various implementations of scintillator x-ray detectors coupled to readout circuitry with an attached power and communication link are known in the x-ray detector art (see Nelson, U.S. patent application Ser. No. 12/384,459) including commercial intraoral dental x-ray cameras.

Figure 9C:
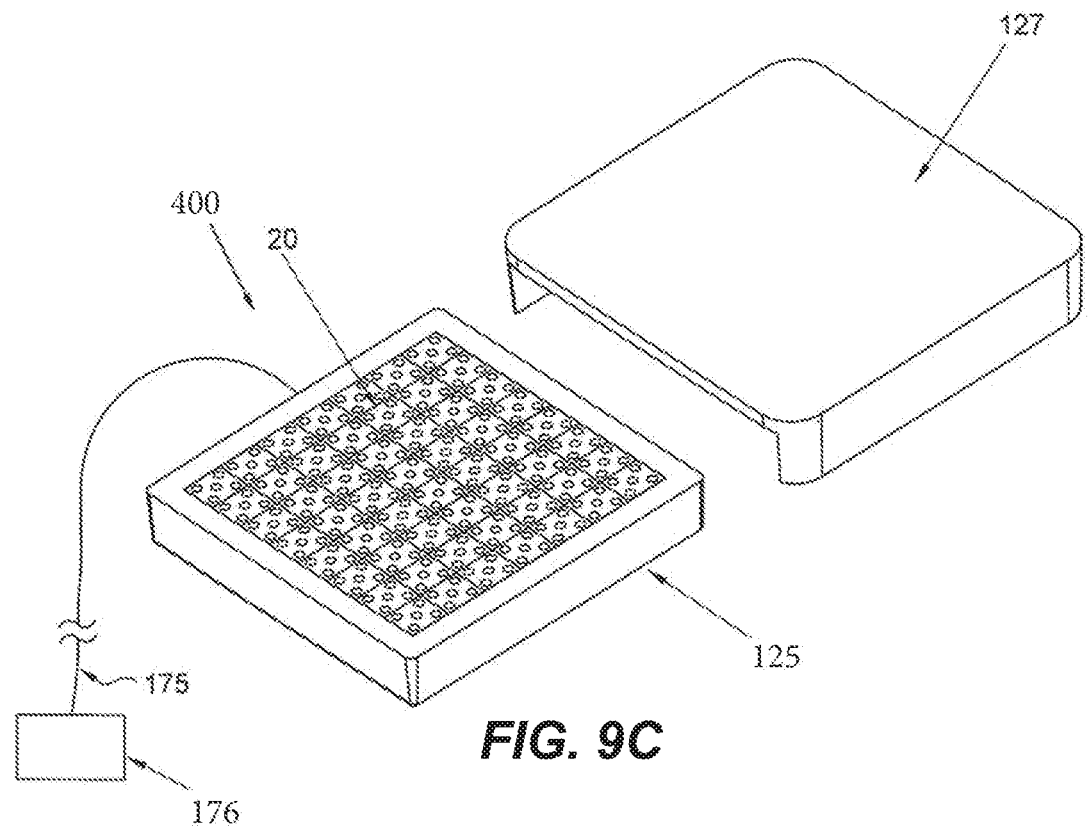
FIG. 9C illustrates a perspective view of a movable protective cover that slides onto a protective frame holding a semiconductor conductive mold x-ray detector with an attached substrate incorporating readout circuitry including a power and communication link.

FIG. 9C illustrates a perspective view of a movable protective cover 127 that can slide onto the protective frame 125 holding a semiconductor structured conductive mold x-ray detector 400 with holes 120 and attached substrate incorporating readout circuitry as well as a power and communication link 175 connected to a computer 176. Alternatively, protective frame 125 can hold a semiconductor structured conductive mold x-ray detector with channels 121. A related implementation of a protective frame and sliding cover for a nano-particle storage phosphor plate x-ray detector is shown in FIG. 5.

Figure 9D:
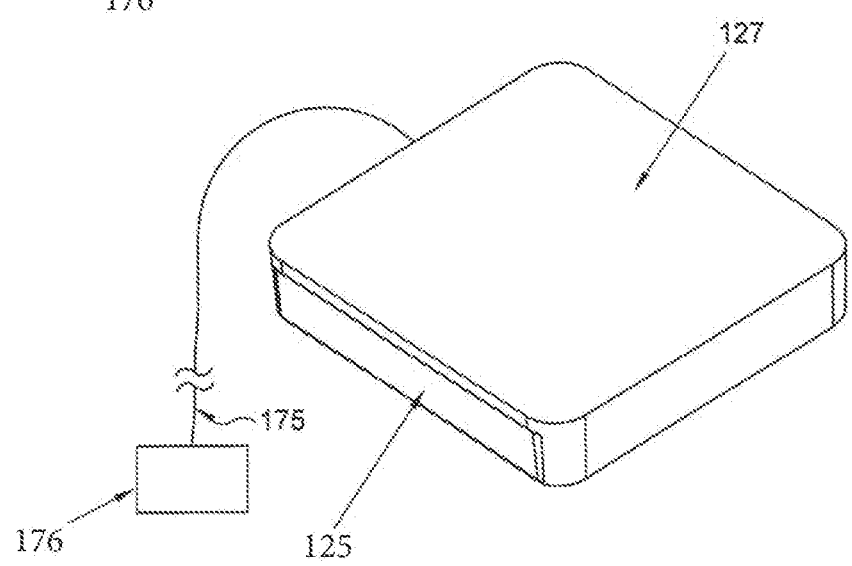
FIG. 9D illustrates a perspective view of a movable protective cover in place over the protective frame holding a semiconductor conductive mold x-ray detector and attached substrate incorporating readout circuitry forming a digital x-ray camera for intraoral dental imaging with a power and communication link connected to computer.

FIG. 9D illustrates a perspective view of a movable protective cover 127 in place over the protective frame 125 forming a digital x-ray camera for intraoral dental imaging with a power and communication link 175 connected to a computer 176.

The invention Literature references expressly incorporated by reference:
KODAK, http://www.kodakdental.com.
Barbaric et al., High Efficiency X-Radiation Converters, U.S. Pat. No. 4,560,882.
Nelson, X-ray Detector for Radiographic Imaging, U.S. Pat. No. 4,937,453.
Nelson, X-ray Detector for Radiographic Imaging, U.S. Pat. No. 5,017,782.
Nelson, Method for Manufacturing a High Resolution Structured X-ray Detector, U.S. Pat. No. 5,258,145.
Nelson et al., Slit and Slot Scan, SAR, and Compton Devices and Systems for Radiation Imaging, U.S. patent application Ser. No. 12/384,459, filed Apr. 6, 2009 (U.S. Pat. No. 8,017,906).
Turner, James E, Atoms, Radiation, and Radiation Protection, 3rd ed. (2007), Wiley-VCR Verlag GmbH & Co. KGaA, Weinheim, ISBN 978-3-527-40606-7.
Rowlands J., Phys. Med. Biol. 47, pp. 123-166 (2002).
Edgar A., et al., Current Applied Physics 6, pp. 399-402 (2006).
Chen G., et al., Journal of Non-crystalline Solids 352, pp. 610-614 (2006).
Johnson J., Schweizer S, J. Am. Ceram. Soc. 90 3, pp. 693-698 (2007).

While the invention is susceptible to various modifications and alternative forms, specific examples thereof have been shown by way of example in the drawings and are herein described in detail. It should be understood, however, that the invention is not to be limited to the particular forms or methods disclosed, but to the contrary, the invention is to cover all modifications, equivalents, and alternatives falling within the spirit and scope of the appended claims.

The invention provides methods and apparatus for detecting radiation including x-ray photon (including gamma ray photon) and particle radiation for dental x-ray imaging, radiation monitoring, and related industrial and scientific applications. Flat or shaped small (and small hybrid) area storage phosphor plates, incorporated with a protective frame and a movable front protective layer are available in multiple sizes, are encased in SP-carriers and used as detectors for intraoral dental x-ray imaging as a replacement for analog x-ray film and digital x-ray cameras, offering good detection efficiency, high spatial and contrast resolution, and a wide dynamic range. After removal of the SP-carrier, a small area storage phosphor plate is loaded into a dental storage phosphor scanner for readout. Intermediate and large area storage phosphor plates (including hybrid versions) are suitable for non-intraoral dental x-ray imaging. Suitable storage phosphors may be used in radiation monitoring, replacing current detectors employed in a film badge format Simple external readers or electronic SP-carriers can provide data readout and thus enable dosimetry.

The invention claimed is:

1. A digital x-ray camera for intraoral dental x-ray imaging comprising:
   a semiconductor structured conductive mold intraoral dental x-ray detector that implements an array of discrete conductive structures including an array of holes or an array of channels with one or more dimensions, wherein the array of holes or the array of channels with one or more dimensions are filled with at least one of polycrystalline, amorphous, or nano-particle semiconductor x-ray converter materials,
   readout electronics configured for acquiring and analyzing readout signals from the semiconductor conductive structured mold intraoral dental x-ray detector implementing the array of holes or array of channels with one or more dimensions, wherein the readout electronics operate in a signal integration mode, a photon detecting mode, or a photon detecting mode with energy resolution;
   a protective shell that encapsulates the semiconductor structured conductive mold intraoral dental x-ray detector and readout electronics; and
   a power source and communications link adapted for connecting to a computer system configured for image data processing and storage of the readout signals, with a display configured for electronic display of the image data processed from the readout signals.

2. A detector system comprising:
   a semiconductor structured conductive mold x-ray or gamma ray detector with an array of discrete conductive structures comprising holes or channels with one or more dimensions, wherein the array of holes or channels with one or more dimensions are filled with at least one of polycrystalline, amorphous, or nano-particle semiconductor x-ray and gamma ray converter materials;
   a substrate with readout electronics configured for acquiring and analyzing readout signals from the semiconductor conductive structured mold x-ray or gamma ray detector, wherein the readout electronics operate in a signal integration mode, a photon detecting mode, or a photon detecting mode with energy resolution; and a communications link adapted for connecting to a computer system configured for image data processing and storage of the readout signals, with a display configured for electronic display of the image data processed from the readout signals.

3. A detector system comprising:

a hybrid semiconductor structured conductive mold x-ray or gamma ray detector implemented with an array of conductive structures including segmented holes or segmented channels with one or more dimensions, wherein the holes or channels are filled with at least one of polycrystalline, amorphous, or nano-particle semiconductor x-ray and gamma ray converter materials;

a substrate with readout electronics configured for acquiring and analyzing readout signals from the semiconductor conductive structured mold intraoral dental x-ray detector, wherein the holes or channels are electronically connected to the substrate and the readout electronics operate in a signal integration mode, a photon detecting mode, or a photon detecting mode with energy resolution;

a communications link adapted to connect the detector system to a computer processor configured for image data processing and storage of the readout signals, with a display configured for electronic display of the image data processed from the readout signals.

4. The digital x-ray camera of claim 1, further comprising a substrate incorporating the readout electronics, wherein the array of holes or the array of channels is electronically connected to the substrate.

5. The digital x-ray camera of claim 1, wherein the communications link is configured for wired or wireless data transfer to the computer system.

6. The digital x-ray camera of claim 1, wherein the semiconductor structured conductive mold intraoral dental x-ray detector is divided into an array of pixels.

7. The digital x-ray camera of claim 6, wherein the array of holes or the array of channels is formed in the pixels and the one or more dimensions comprise a hole dimension or channel dimension of the respective holes or channels, which is smaller than the pixels.

8. The digital x-ray camera of claim 6, wherein the pixels are formed of or comprise a semiconductor detector material adapted to detect x-ray and gamma ray photons.

9. The digital x-ray camera of claim 1, wherein the protective shell comprises a frame with an optically opaque, x-ray transmissive cover adapted for positioning in a patient's mouth.

10. The detector system of claim 2, wherein the communications link is configured for wired or wireless data transfer to the computer system.

11. The detector system of claim 2, wherein the semiconductor structured conductive mold x-ray or gamma detector is divided into an array of pixels.

12. The detector system of claim 11, wherein the array of holes or channels is formed in the pixels and electronically connected to the substrate, and wherein the one or more dimensions comprise a hole dimension or channel dimension of the respective holes or channels, which is smaller than the respective pixels.

13. The detector system of claim 11, wherein the pixels are formed of or comprise a semiconductor material adapted to detect x-ray and gamma ray photons.

14. The detector system of claim 2, wherein the semiconductor structured conductive mold x-ray or gamma detector is mounted in a frame with an optically opaque, x-ray transmissive cover adapted for positioning in a patient's mouth.

15. The detector system of claim 2, wherein the semiconductor structured conductive mold x-ray or gamma ray detector is configured for non-intraoral imaging.

16. The detector system of claim 3, wherein the communications link is configured for wired or wireless data transfer to the computer processor.

17. The detector system of claim 3, wherein the hybrid semiconductor structured conductive mold x-ray or gamma detector is divided into an array of pixels in which the array of holes or channels is formed, and wherein the one or more dimensions comprise a hole dimension or channel dimension of the respective holes or channels, which is smaller than the pixels.

18. The detector system of claim 17, wherein the pixels are formed of or comprise a semiconductor material adapted to detect-ray and gamma ray photons.

19. The detector system of claim 3, wherein the hybrid semiconductor structured conductive mold x-ray or gamma detector is mounted in a frame with an optically opaque, x-ray transmissive cover adapted for positioning in a patient's mouth.

20. The detector system of claim 3, wherein the hybrid semiconductor structured conductive mold x-ray or gamma ray detector is configured for non-intraoral imaging.

* * * * *